United States Patent
Findlay et al.

(10) Patent No.: US 9,720,220 B2
(45) Date of Patent: Aug. 1, 2017

(54) TOMOGRAPHY ACCESSORY DEVICE FOR MICROSCOPES

(71) Applicant: University of Manitoba, Winnipeg (CA)

(72) Inventors: Catherine Rui Jin Findlay, Winnipeg (CA); Kathleen Margaret Gough, Winnipeg (CA)

(*) Notice: Subject to any disclaimer, the term of this patent is extended or adjusted under 35 U.S.C. 154(b) by 23 days.

(21) Appl. No.: 15/065,379

(22) Filed: Mar. 9, 2016

(65) Prior Publication Data

US 2016/0266363 A1    Sep. 15, 2016

Related U.S. Application Data

(60) Provisional application No. 62/131,655, filed on Mar. 11, 2015.

(51) Int. Cl.
   *G02B 21/26*     (2006.01)
   *G01N 21/35*     (2014.01)
   *G01N 21/17*     (2006.01)

(52) U.S. Cl.
   CPC .......... *G02B 21/26* (2013.01); *G01N 21/35* (2013.01); *G01N 2021/1787* (2013.01)

(58) Field of Classification Search
   CPC .. G02B 21/00; G02B 21/004; G02B 21/0024; G02B 21/0028; G02B 21/24; G02B 21/26
   USPC .................. 359/391, 392, 393, 394
   See application file for complete search history.

(56) References Cited

U.S. PATENT DOCUMENTS

| | | | | |
|---|---|---|---|---|
| 3,629,577 A | * | 12/1971 | Weber ................. | H01J 37/20 250/307 |
| 5,264,705 A | * | 11/1993 | Honda .................. | H01J 37/20 250/442.11 |
| 2004/0207840 A1 | * | 10/2004 | Sharpe ................ | G01N 21/6458 356/244 |
| 2007/0125958 A1 | * | 6/2007 | Tappel .................. | H01J 37/20 250/441.11 |
| 2007/0231785 A1 | * | 10/2007 | Hoyt .................... | G01N 21/23 435/4 |
| 2011/0253905 A1 | * | 10/2011 | Moebus ................. | G21K 7/00 250/441.11 |

* cited by examiner

*Primary Examiner* — Arnel C Lavarias
(74) *Attorney, Agent, or Firm* — Ryan W. Dupuis; Kyle R. Satterthwaite; Ade & Company Inc.

(57) ABSTRACT

A tomography accessory device for supporting a sample relative to the imaging assembly of a microscope has an electric positioning motor supported on the existing sample supporting stage of the microscope. An output shaft of the positioning motor is supported for rotation about an output axis parallel to a plane of the stage and a controller acts to control the motor so as to rotate the output shaft between a plurality of different angular positions about the output axis. An adjustable assembly supports a sample holder relative to the outer shaft such that i) the sample holder is translatable relative to the output shaft along at least one translation axis oriented generally perpendicularly to the output axis, and ii) the sample holder is pivotable relative to the output shaft about at least two pivot axes which are transverse to one another and which are generally perpendicular to the output axis.

10 Claims, 4 Drawing Sheets

US 9,720,220 B2

TOMOGRAPHY ACCESSORY DEVICE FOR MICROSCOPES

This application claims the benefit under 35 U.S.C. 119(e) of U.S. provisional application Ser. No. 62/131,655, filed Mar. 11, 2015.

FIELD OF THE INVENTION

This invention is a lightweight, micromechanical, motorized device designed to be mounted directly onto a microscope stage for the purpose of holding, aligning and rotating a sample with the precise degrees of control required for Infrared (IR) tomography of microscopic samples.

BACKGROUND

The original idea and demonstration of tomographic infrared imaging was published in Nature Methods 10:861-866 (2013), to world-wide interest. Despite interest and potential application in multiple disciplines, 3D infrared imaging experiments were published only at the InfraRed Environmental Imaging beam line (IRENI, Synchrotron Radiation Center, Stoughton, Wis.) as described in Nature Methods 2013; SRC was decommissioned in March 2014. The experiment designed for IRENI was physically feasible because IRENI offered sufficient spatial resolution and sufficient brightness with the synchrotron source. It is believed that the experiment has not been repeated because of physical limitations with the system described in Nature Methods 2013. Their goniometer/holder stands off the microscope stage, requiring removal of the stage for 3D imaging. Over time, the dismount/remount of the stage resulted in loss of stage control and performance (accuracy, precision and reproducibility) for 2D image acquisition. Device parts for IRENI were expensive (e.g. near $10,000), yet positioning control was inadequate: the arrangement did not have enough degrees of freedom to straighten a long sample and align it along the axis of rotation. Removal of the motorized microscope stage also removed the possibility of obtaining a series of images in the same plane (a.k.a. mosaic mode).

SUMMARY OF THE INVENTION

The present invention seeks to improve upon some of the deficiencies of the prior art, in that the present invention delivers 3D imaging as single tiles or mosaics, in the form of a light-weight ready-to-go accessory paired with a software package, at a fraction of the cost associated with the published installation, making infrared tomography feasible with more IR microscopes, employing a variety of light sources, without removal of the motorized stage, if one is present, or interference with normal functionality. The device can be rapidly installed and uninstalled to restore full 2D imaging capability. Although well suited for use with FTIR microscopes, there are other instruments that do not require the FT process of Michelson interferometer, but can accommodate the current device. Also, the device is not necessarily restricted to use with infrared wavelengths. A visible movie can be captured from the microscope camera of the microscope too.

According to one aspect of the invention there is provided a tomography accessory device for use with a microscope comprising an imaging assembly having an objective and a condenser lens and a sample supporting stage supported between the objective and the condenser lens, the device comprising:

a) an electric motor for being supported on the stage and having an output shaft supported for rotation about an output axis parallel to a plane of the stage;
b) a controller for controlling operation of electric motor to rotate the output shaft between a plurality of different angular positions about the output axis;
c) a sample holder for supporting a sample to be imaged thereon; and
d) an adjustable assembly for supporting the sample holder on the output shaft of the electric motor such that: i) the sample holder is translatable relative to the output shaft along at least one translation axis oriented generally perpendicularly to the output axis, and ii) the sample holder is pivotable relative to the output shaft about at least two pivot axes which are transverse to one another and which are generally perpendicular to the output axis.

Preferably the two translation axes are perpendicular to one another.

Preferably the adjustable assembly also supports the sample holder such that the sample holder is translatable relative to the output shaft along two translation axes which are transverse to one another and which are generally perpendicular to one another.

The adjustable assembly may include a first positioning assembly comprising two bodies which are coupled to as to be pivotal relative to one another about a first one of the pivotal axes and translatable relative to one another along a first one of the translation axes.

The adjustable assembly may further include a second positioning assembly comprising two bodies which are coupled to as to be pivotal relative to one another about a second one of the pivotal axes and translatable relative to one another along a second one of the translation axes.

Preferably one of the bodies of the second positioning assembly is fixed relative to one of the bodies of the first positioning assembly.

According to a second aspect of the present invention there is provided a method of imaging a sample using a microscope comprising an imaging assembly having an objective and a condenser lens and a sample supporting stage supported between the objective and the condenser lens, the method comprising:

a) providing a tomography accessory device including i) an electric motor having an output shaft, ii) a sample holder, and iii) an adjustable assembly supporting the sample holder on the output shaft;
b) supporting the electric motor on the stage of the microscope such that the output shaft is supported for rotation about an output axis parallel to a plane of the stage;
c) supporting the sample to be imaged on the sample holder;
d) adjusting the sample holder relative to the output axis by enabling the sample holder to be i) translatable relative to the output shaft along at least one translation axis oriented generally perpendicularly to the output axis, and ii) pivotable relative to the output shaft about at least two pivot axes which are transverse to one another and which are generally perpendicular to the output axis; and
e) controlling operation of electric motor to rotate the output shaft between a plurality of different angular positions about the output axis as the imaging assembly captures images of the sample.

Preferably the tomography accessory device is supported on the stage of the microscope such that: i) the tomography accessory device is readily removable from the stage of the microscope, and/or ii) the tomography accessory device is movable together with the stage of the microscope relative to the imaging assembly of the microscope.

According to the preferred embodiment, the device comprises a miniature electric motor to provide rotation and mechanical parts to position the long central axis of the sample such that it is centred and aligned with the axis of rotation, under the objective and over the condenser lens on an infrared microscope in transmission mode, in the plane of focus. The part of the device that rests on an infrared microscope stage has minimal weight, so as not to cause damage to these precisely machined, expensive stages. Miniature mechanical components include wrist action positioners. The sample can be adjusted for tilt and its centre of rotation can be adjusted with multiple degrees of freedom. The device has control systems and circuitry that allow it to rotate in synchronization with the automated acquisition of images at different viewing angles, for tomography. More particularly, the sample rotates in between acquisition of 2 sequential images, not during the acquisition of an individual image.

This device is designed to be miniaturized, lightweight, and to have all the degrees of freedom required to position an object, for example any regular or irregular object, whether long or short, cylindrical or oblong, or spherical, to be aligned straight with respect to acquired images and to have all parts lie within the depth of field of the microscope optics.

In comparison to the only existing device, this miniaturized, lightweight device can rest on, or be attached to, a microscope stage, without affecting the proper performance of the stage, regardless of whether the stage positioning is motorized or manually controlled.

Due to the low profile and miniaturization of its design, the tomography device can be used without reconfiguration or removal of the microscope stage in order to create clearance for rotation equipment. The device can be mounted and dismounted with ease and speed, without disrupting the normal stage operation and without incurring long term damage to accuracy and precision of motorized stage.

Samples that extend beyond the single tile image area can be viewed via multi-tile imaging via the now-enabled stage raster scanning capability. With this invention, applications of infrared tomography are expanded beyond those shown previously, that is, samples that fit within the one tile imaged onto the FPA detector.

This device is unique in that it is the first and only miniaturized, inexpensive and lightweight infrared tomographic device that can rest on or be affixed to the stage, and that is accompanied by customized software with combined original operational features for data collection and analysis.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
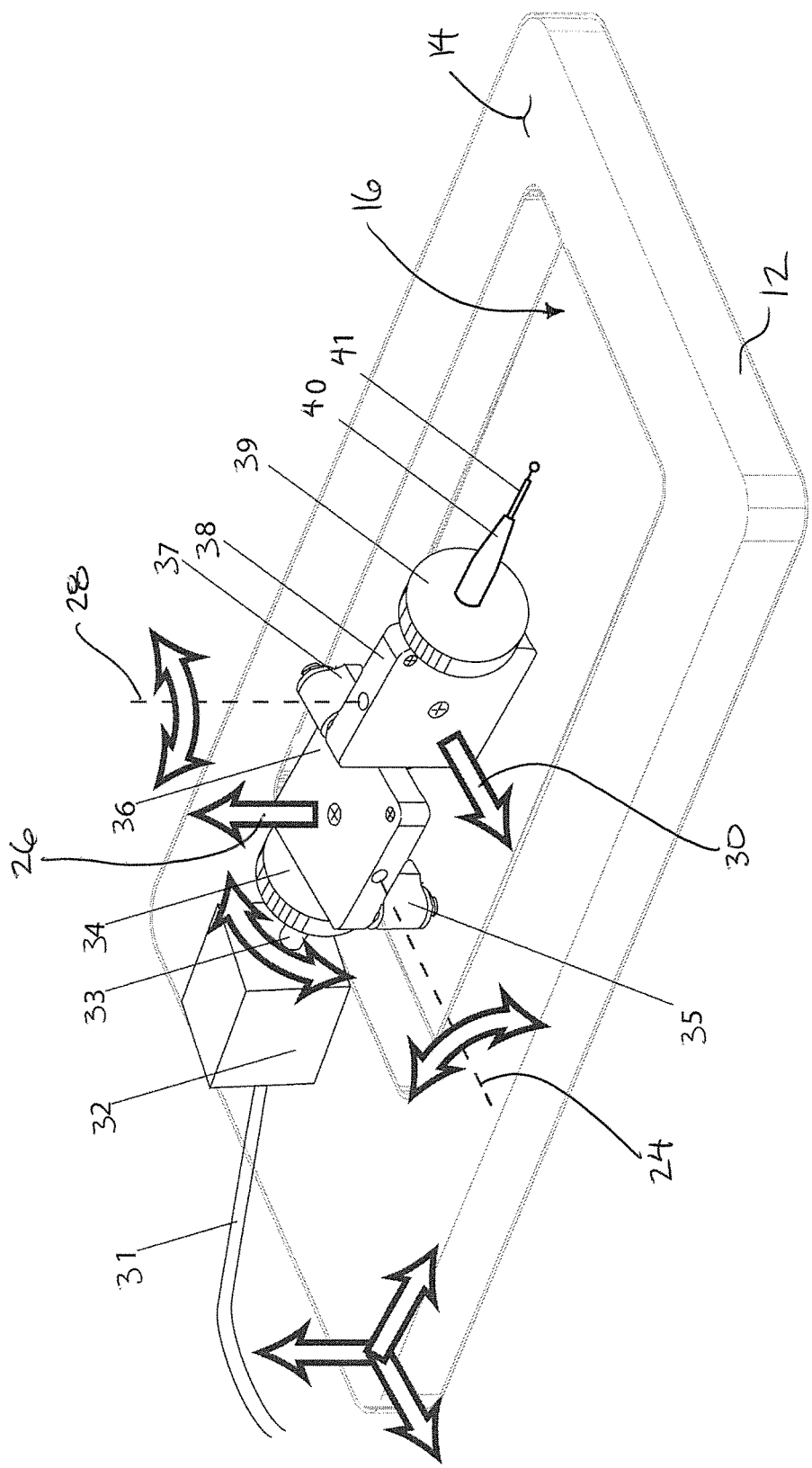
FIG. 1 is a perspective view of the tomography accessory device supported on a microscope stage.
Figure 2:
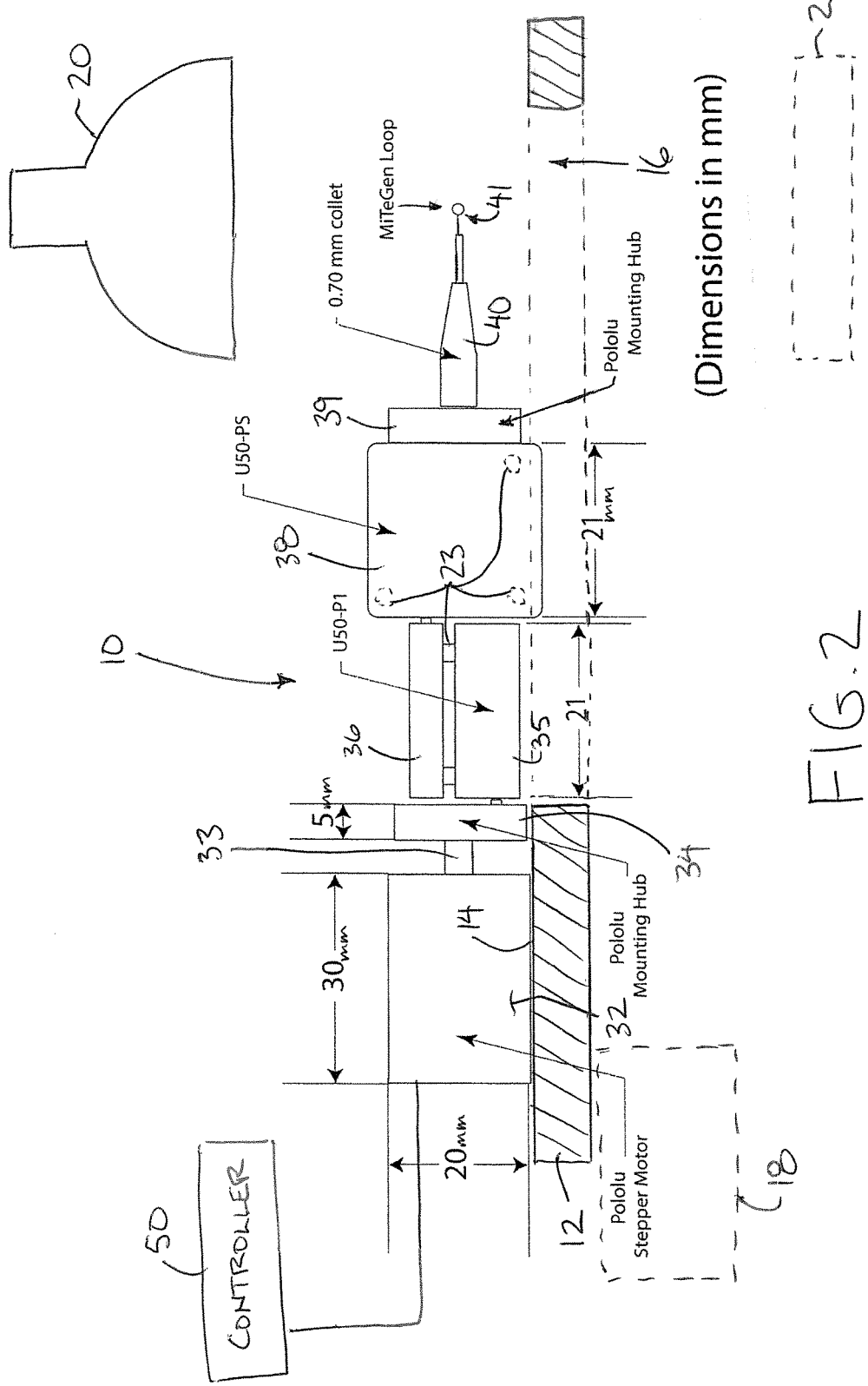
FIG. 2 is an elevational view of the tomography accessory device supported on a microscope stage.
Figure 3:
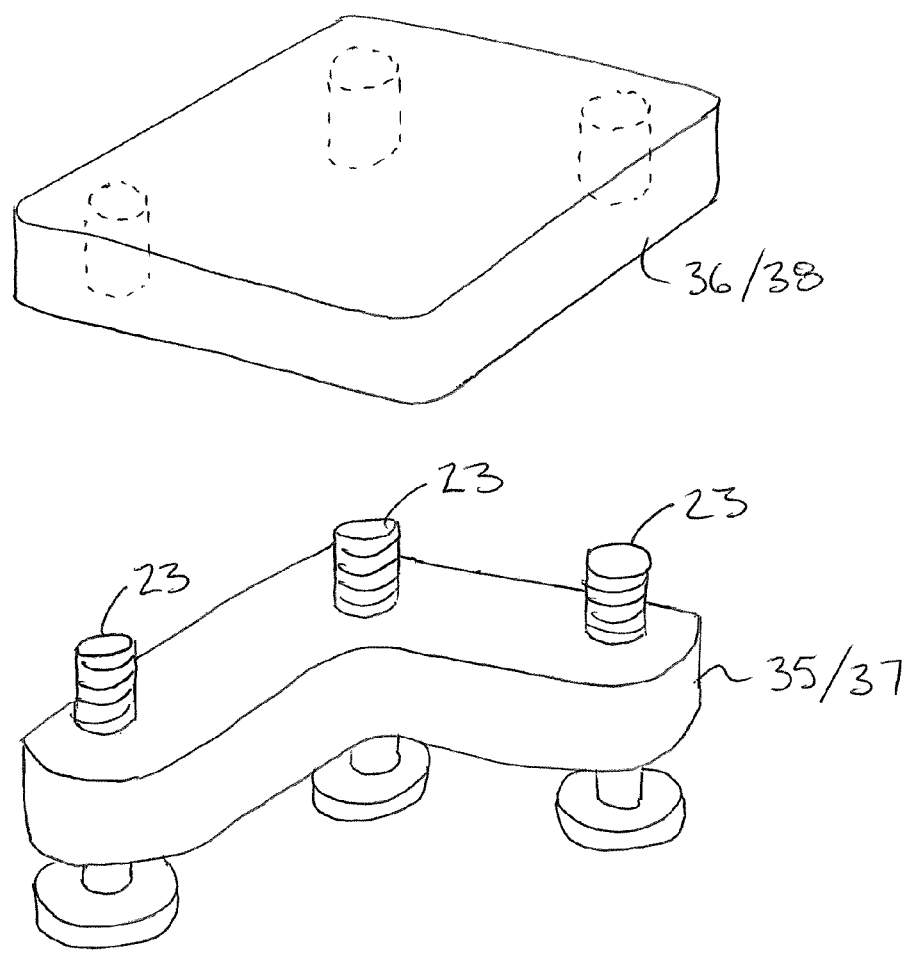
FIG. 3 is an exploded perspective view of the first and second positioning assemblies.

Referring to the accompanying figures, there is illustrated a tomography accessory device generally indicated by reference numeral 10. The device 10 is particularly suited for use with a microscope in performing three dimensional spectral imaging.

The microscope typically comprises an infrared microscope having a stage 12 for supporting a sample thereon to be imaged by the imaging assembly of the microscope. In the illustrated embodiment, the stage 12 comprises a platform having a horizontal upper surface 14 defining a plane of the stage. The platform is a rectangular frame for extending about the rectangular perimeter of a central opening 16 of the stage 12.

A motorized support 18 controllably displaces the stage relative to the imaging assembly of the microscope to permit the stage to be translated along two horizontal axes which are perpendicular to one another. The motorized support also controllably adjusts the height of the stage relative to the imaging assembly for translation along a third vertical axis.

The imaging assembly of the microscope typically includes an objective 20 supported above the stage 12 and a condenser lens 22 below the stage which are aligned with the central opening 16 in the stage for imaging a sample suspended above the central opening.

The accessory device 10 serves to support a sample relative to the stage such that the sample supporting portion of the device is movable together with the stage under control of the motorized support 18 for controlling the position of the sample supporting portion of the accessory device 10 relative to the imaging assembly in the usual manner of controlling the stage positioning.

The accessory device 10 includes a stepper motor 32 which is sufficiently small in size to permit being supported on the upper surface 14 of the stage offset to one end of the central opening 16. The stepper motor 32 includes an output shaft 33 projecting towards the central opening 16 such that the output shaft is rotatable about a respective longitudinal axis which is horizontal and parallel to the upper surface 14 at a location spaced slightly thereabove.

A hub 34 is mounted on the output shaft and serves to support a first positioning assembly on the outer end thereof. The first positioning assembly includes a first plate 35 fixed relative to the hub 34 and a second plate 36 mounted in proximity to the first plate such that the plates are near parallel to one another and spaced apart from one another, but are adjustable relative to one another as described in further detail in the following.

The second plate 36 is a generally rectangular plate coupled to the first plate by three screws 23 which are received in threaded connection within respective sockets at three corners of the rectangular plate. The three screws are thus located in a generally triangular pattern relative to one another.

The first plate 35 rotatably supports each screw thereon to form the connection between the two plates. Two innermost screws closest to the motor lie in a generally common plane which is near perpendicular to the output axis of the stepper motor, while the third screw is spaced axially from the two innermost screws so as to be rotatable about a respective axis which is near parallel and spaced longitudinally from the two innermost screws.

Rotating the outermost screw in rotatable connection to the first plate and in threaded connection to the second plate allows the spacing between the plates at the location of the third screw to be adjusted. By adjusting only the outermost screw, the second plate is effectively tilted relative to the first plate about a first pivotal axis 24 which is near perpendicular to the output axis of the stepper motor. Alternatively, if one were to adjust all three screws 23 by equal increments, the second plate would be translated relative to the first plate in the direction of a first translation axis 26 which is near perpendicular to the first pivotal axis and which is transverse to the output axis in near perpendicular relation thereto.

A second positioning assembly is similarly provided in the form of a first plate 37 fixed to the second plate 36 of the first positioning assembly, and a second plate 38 which is adjustably supported relative to the first plate. The second positioning assembly is substantially identical to the first position assembly with the only exception being that adjustment of the outermost screw 23 alone causes tilting movement of the second plate relative to the first plate about a second pivotal axis 28 which is generally perpendicular to the first pivotal axis 24 and generally perpendicular to the output axis of the stepper motor. Also, similar to the first positioning assembly, adjustment of all three screws 23 of the second positioning assembly by identical increments causes the second plate 38 to be displaced relative to the first plate 37 in a translating movement along a second translating axis 30 which is near perpendicular to the first translating axis and to the output axis.

A hub 39 is mounted in fixed relation to the second plate of the second positioning assembly such that the hub is positionable relative to the output axis of the stepper motor about both pivotal axes and along both translating axes.

A collet 40 is mounted to the hub to support a sample holder 41 therein of the type formed of a strand material, for example a plastic strand or a metal wire. In the preferred embodiment, the sample holder is a polyamide loop with a stem connected to the loop that is received within the collet.

Figure 4:
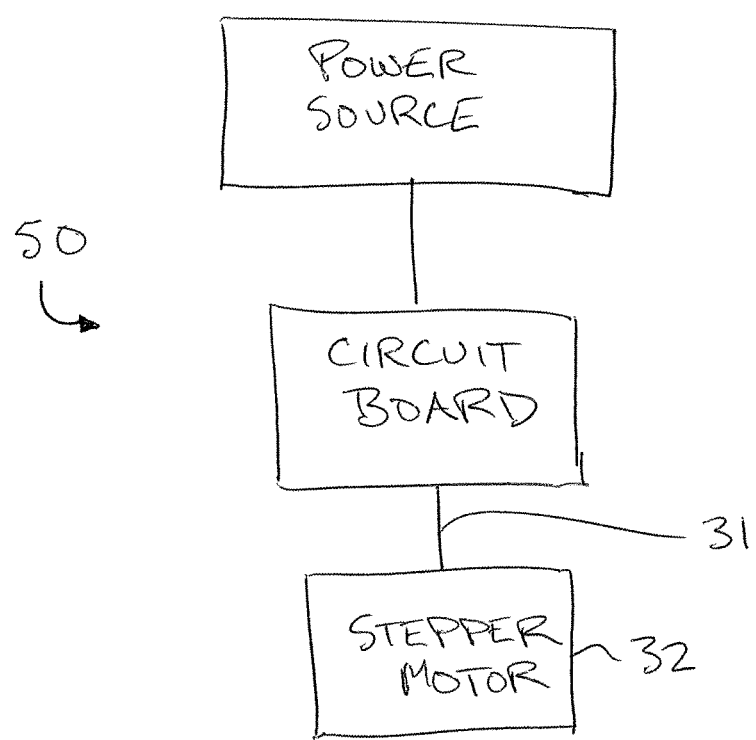
FIG. 4 is a representation of the controller which drives the motor.

The accessory device 10 further includes a controller 50 which is supported separately from the stage 12 and which is connected to the stepper motor 32 by suitable wiring 31 for driving the stepper motor 32. Details of the controller are illustrated in FIG. 4. Typically the controller 50 functions to drive the rotation of the stepper motor between different positions which are angularly offset from one another by selected increments of rotation about the output axis of the motor.

The accessory device 10 is typically supported on the existing stage 12 of the microscope to remain readily separable therefrom such that the stage 12 remains functional for other uses. When it is desirable to use the infrared microscope for three dimensional spectral imaging, the stepper motor is supported on the stage and a sample to be imaged is supported by the sample holder 41. The sample holder is adjusted relative to the output axis by relative pivotal movement and relative translating movement along the two pivot axes and the two translating axes until the sample is generally centered coaxially with the output axis of the stepper motor and the geometry of the sample is aligned with the axis of rotation defined by the output shaft of the stepper motor.

In the instances where a sample is larger than a single imaging tile of the microscope, the conventional motorized controls 18 of the microscope stage 12 can be used to translate the entire accessory device 10 with the sample supported thereon on the stage 12 relative to the imaging assembly for performing multi-tile imaging in the conventional manner.

The following components are shown in the accompanying figures:

31. Stepper motor wires connecting to microcontroller (Arduino Uno) and motor driver (Adafruit Motor Shield)
32. Body of stepper motor (Stepper Motor: Bipolar, 200 Steps/Rev). Fixed to microscope stage.
33. Shaft of Stepper motor, rotates with respect to 32.
34. Mounting Hub (Pololu Universal Aluminum Mounting Hub for 4 mm Shaft), fixed to 33.
35. Bottom plate of first two plate adjustment system (U50-PS, Newport), fixed to 34.
36. Top plate of first 2 plate system, connected to 35, but position adjusted with screws (80 turns per inch). Can translate with respect to 35 Can also tilt with respect to 35.
37. Bottom plate of second two plate adjustment system, fixed to 36 at 90 degrees.
38. Top plate of second two plate adjustment system, connected to 37 with position adjusted with screws. Can translate and tilt with respect to 37.
39. Mounting Hub, fixed to 38.
40. Collet (0.7 mm from mechanical pencil), fixed to 39.
41. MiTeGen polyamide loop used to hold samples (example, diatom cells). Wire from staples also works for other samples (example, spider silk).

NOTE: The microscopic sample, fixed to the end of 41, needs to be positioned in a specific spot in space. The sample needs to rotate around its long axis. Sample position in x and y needs to be within the field of view captured in an image (about 70 microns for high resolution IR microscopes). The samples z position should be within the depth of field of the microscope (about 10 microns for mid infrared light). Cylindrical sample must be in focus (within depth of field) at all points along its length.

The shaft of the stepper motor should be parallel to stage, and cannot be any higher above the stage than allowed for by the working distance for microscope and the up and down range of movement of the stage. (21 mm for the 620/670 Cary IR microscope)

The stepper motor needs to have as at least as many non-redundant (not 180 degrees from another) steps per revolution as there are pixels along one edge of IR image (e.g. 64 for Agilent 620/670 in-house at U of Manitoba).

Potential commercial applications include, but are not limited to, 3D imaging of samples of all types such as naturally occurring organic samples (e.g.: cells, diatoms, fungi, spores, seeds, hair, fibres, spider silk), manufactured organic samples (e.g.: protein and other crystals, simulated biological fibres, synthetic threads) or inorganic samples (e.g.: minerals, paint chips, polymers). All molecular structures exhibit unique signatures, or infrared fingerprints, that can be imaged and analysed.

The accessory can be equipped with a rotational encoder for feedback of rotational travel data recorded by computer via software.

The accessory can rest on one point of the stage with the sample projecting into the field of view of the microscope. The rotational encoder can be on the same side of the sample as the motor. Alternatively, the accessory can rest at two points and extend to the side of the sample, and can have additional support. The rotational encoder could then be on the opposite side of the sample as the motor.

Samples such as fibres, threads or hairs, could be gripped at the opposite end with a second gripping, positioning, rotating device, such that the sample could be supported, twisted or stretched, to monitor the variation in IR signature with rotation and tensile stress. Alternatively, a device that achieves all of these features, but has an extended gripping attachment (elongated) could actually be locked beside the stage, rather than attached to the stage.

The device is used in combination with our customized, Matlab™ based software that imports, processes and integrates 2D infrared images in batches and performs back projection and reconstruction to form 3D infrared images. It displays and exports the 3D voxelized images and can display and export movies of the 3D display viewed while rotating. We use a particular file structure and the file extension (*.3DIR) with our software.

There is currently no single piece of software available that completely performs all the processing for infrared tomography, other than our software. Other programs, such as the ResolutionsPro proprietary software with the Agilent system, enables some parts of the processing required (that is, integration of area under an absorbance peak), but not the remaining tomographic reconstruction tasks. Our software uses the integrated peak areas as inputs for reconstruction and back projection algorithms, unlike others.

Since various modifications can be made in my invention as herein above described, it is intended that all matter contained in the accompanying specification shall be interpreted as illustrative only and not in a limiting sense.

The invention claimed is:

1. A tomography accessory device for use with a microscope comprising an imaging assembly having an objective and a condenser lens and a sample supporting stage supported between the objective and the condenser lens, the device comprising:
    an electric motor for being supported on the stage and having an output shaft supported for rotation about an output axis parallel to a plane of the stage;
    a controller for controlling operation of electric motor to rotate the output shaft between a plurality of different angular positions about the output axis;
    a sample holder for supporting a sample to be imaged thereon; and
    an adjustable assembly for supporting the sample holder on the output shaft of the electric motor such that:
    the sample holder is translatable relative to the output shaft along at least one translation axis oriented generally perpendicularly to the output axis; and
    the sample holder is pivotable relative to the output shaft about at least two pivot axes which are transverse to one another and which are generally perpendicular to the output axis.

2. The device according to claim 1 wherein the two pivot axes are perpendicular to one another.

3. The device according to claim 1 wherein the adjustable assembly supports the sample holder such that the sample holder is translatable relative to the output shaft along two translation axes which are transverse to one another and which are generally perpendicular to one another.

4. The device according to claim 3 wherein the two translation axes are perpendicular to one another.

5. The device according to claim 3 wherein the adjustable assembly includes a first positioning assembly comprising two bodies which are coupled to as to be pivotal relative to one another about a first one of the pivotal axes and translatable relative to one another along a first one of the translation axes.

6. The device according to claim 5 wherein the adjustable assembly further includes a second positioning assembly comprising two bodies which are coupled to as to be pivotal relative to one another about a second one of the pivotal axes and translatable relative to one another along a second one of the translation axes.

7. The device according to claim 6 wherein one of the bodies of the second positioning assembly is fixed relative to one of the bodies of the first positioning assembly.

8. A method of imaging a sample using a microscope comprising an imaging assembly having an objective and a condenser lens and a sample supporting stage supported between the objective and the condenser lens, the method comprising:
    providing a tomography accessory device including i) an electric motor having an output shaft, ii) a sample holder, and iii) an adjustable assembly supporting the sample holder on the output shaft;
    supporting the electric motor on the stage of the microscope such that the output shaft is supported for rotation about an output axis parallel to a plane of the stage;
    supporting the sample to be imaged on the sample holder; and
    adjusting the sample holder relative to the output axis by enabling the sample holder to be i) translatable relative to the output shaft along at least one translation axis oriented generally perpendicularly to the output axis, and ii) pivotable relative to the output shaft about at least two pivot axes which are transverse to one another and which are generally perpendicular to the output axis;
    controlling operation of electric motor to rotate the output shaft between a plurality of different angular positions about the output axis as the imaging assembly captures images of the sample.

9. The method according to claim 8 including supporting the tomography accessory device on the stage of the microscope such that the tomography accessory device is readily removable from the stage of the microscope.

10. The method according to claim 8 including supporting the tomography accessory device on the stage of the microscope such that the tomography accessory device is movable together with the stage of the microscope relative to the imaging assembly of the microscope.

* * * * *